(12) United States Patent
Pagani

(10) Patent No.: US 6,287,525 B1
(45) Date of Patent: Sep. 11, 2001

(54) PROCESS AND PLANT FOR UREA PRODUCTION WITH REACTION SPACES HAVING DIFFERENTIATED YIELDS

(75) Inventor: Giorgio Pagani, Lugano (CH)

(73) Assignee: Urea Casale, Lugano-Besso ( * ) Notice: Subject to any disclaimer, the term of this patent is extended or adjusted under 35 U.S.C. 154(b) by 0 days.

(21) Appl. No.: 08/860,324

(22) PCT Filed: Dec. 21, 1995

(86) PCT No.: PCT/EP95/05065

§ 371 Date: Aug. 25, 1997

§ 102(e) Date: Aug. 25, 1997

(87) PCT Pub. No.: WO96/20170

PCT Pub. Date: Jul. 4, 1996

(30) Foreign Application Priority Data

Dec. 23, 1994 (CH) ............................................ 03905/94

(51) Int. Cl.⁷ .................................... B01J 8/04; B01D 1/00
(52) U.S. Cl. ............................ 422/234; 422/189; 564/66; 564/67; 564/69; 564/70; 564/73; 159/47.2
(58) Field of Search .................................. 422/189, 191, 422/196, 234, 187–188; 564/67, 69, 70, 73, 66; 159/47.2; 203/31, 49; 42/359, 358

(56) References Cited

U.S. PATENT DOCUMENTS

| | | | |
|---|---|---|---|
| 2,087,980 | 7/1937 | Lawrence | 564/67 |
| 2,716,629 | * 8/1955 | Kodama et al. | |
| 3,091,637 | 5/1963 | Cook et al. | 564/72 |
| 3,867,442 | * 2/1975 | Logemann | 260/555 |
| 4,061,633 | * 12/1977 | Blyakhman et al. | 544/106 |
| 4,210,600 | 7/1980 | Zardi | 564/71 |
| 4,539,077 | * 9/1985 | Jonckers et al. | 203/49 |
| 5,580,236 | * 12/1996 | Pagani | 422/188 |
| 5,660,801 | * 8/1997 | Pagani et al. | 422/189 |
| 5,681,537 | * 10/1997 | Pagani | 422/191 |

FOREIGN PATENT DOCUMENTS

| | | |
|---|---|---|
| 0544056 | 6/1993 | (EP) . |
| 0598250 | 5/1994 | (EP) . |
| 0611753 | 8/1994 | (EP) . |
| 0624571 | 11/1994 | (EP) . |
| 0479103 | 4/1996 | (EP) . |
| 1573707 | 7/1969 | (FR) . |
| 1124547 | 8/1968 | (GB) . |
| 1217560 | 12/1970 | (GB) . |
| 606858 | 5/1978 | (RU) . |
| 614099 | 7/1978 | (RU) . |

* cited by examiner

Primary Examiner—Marian C. Knode
Assistant Examiner—Alexa A. Doroshenk
(74) Attorney, Agent, or Firm—Sughrue, Mion, Zinn, Macpeak & Seas, PLLC

(57) ABSTRACT

In a process for urea production, substantially pure ammonia and carbon dioxide are reacted in a main reaction space from which outgoes a reaction mixture subjected to stripping to obtain a partially purified mixture sent to a urea recovery section. From this section, a dilute carbamate solution is obtained which is recycled to an auxiliary reaction space in which the residual carbamate is converted into urea. This process achieves high average conversion yield with reduced energy consumption.

27 Claims, 8 Drawing Sheets

PROCESS AND PLANT FOR UREA PRODUCTION WITH REACTION SPACES HAVING DIFFERENTIATED YIELDS

TECHNICAL FIELD

In its general aspect the present invention relates to a method for modernizing a plant for urea production of the type comprising:

a urea synthesis reactor;

a stripping equipment for subjecting a first reaction mixture leaving said reactor to a treatment of partial decomposition of the carbamate and partial separation of the free ammonia in aqueous solution present in said first mixture;

means for condensing at least partially the vapors leaving said stripping equipment and recycling a first carbamate solution to said reactor;

a recovery section for separating the urea produced in said reactor from a second aqueous carbamate solution.

The present invention also relates to a plant for producing urea obtainable by the modernization method of the present invention.

As is known, in the field of urea production the need is ever more growing of plants having greater capacity and operating flexibility on the one hand and, on the other hand, requiring ever smaller investment and operating costs, in particular in energy terms.

BACKGROUND ART

To this end, there have been proposed and implemented in the art a series of urea production processes essentially based on conversion reactions with differentiated yields in reaction spaces placed in parallel as described e.g. in European patent application EP-A-0 479 103.

In these processes, the total urea production is distributed between a main reaction space designed to cover the greater part of the required production capacity (generally from 60% to 80% thereof) and operating under low-yield conditions, and an auxiliary reaction space—so-called "once through"—operating under high-yield conditions and designed to bring production capacity to the final amount required.

Within the framework of the above mentioned processes, the reaction mixture from the main reaction space is subjected to a preliminary purification treatment to obtain a concentrated solution of carbamate recycled to the reaction space and a urea solution which is further processed and purified—together with the reaction mixture leaving the auxiliary reaction space—in a separation and recovery section.

From this latter section, a dilute carbamate solution and a substantially pure urea solution are obtained.

In accordance with the constant teaching of the prior art and for the purpose of increasing as much as possible the conversion yield in the auxiliary reaction space, this space is fed exclusively with substantially pure carbon dioxide and ammonia while the dilute carbamate solution is recycled exclusively to the main reaction space, to which is accordingly delegated the duty of converting into urea all the carbamate obtained in the purification sections located downstream thereof.

Although essentially meeting the above mentioned need, these processes exhibit both a weighted average yield limited by the rather poor yield in the main reactor and a series of plant limitations linked to the need of sending high recycle flowrates to the main reactor and provide an auxiliary reactor of large size and high cost.

The large quantity of water in the recycle solution to the main reaction space, furthermore, poses—despite the high conversion yield of the auxiliary reaction space—an upper limit to the average conversion yield achievable by the plant, which in turn limits the energy savings achievable in terms of high-pressure steam consumption reduction.

As disclosed in European patent applications EP 0 544 056 and EP 0 624 571, also known in the art are processes for the industrial synthesis of urea carried out by brand new plants wherein highly pure ammonia and carbon dioxide are reacted in a first reaction space, while a solution of recycled carbamate coming from an urea recovery section is sent to a second reaction space in which they react with an unreacted portion of ammonia and carbon dioxide.

Neither EP 0 544 056 nor EP 0 624 571, however, afford the problem of modernizing pre-existing urea production plants including a stripping equipment for treating the ureacontaining reaction mixture with the aim of enhancing production capacity while having at the same time a high weighted average yield.

DISCLOSURE OF INVENTION

The technical problem underlying the present invention is accordingly to conceive and make available a method for modernizing a plant for urea production which allows to overcome the drawbacks of the above mentioned prior art.

In accordance with a first embodiment of the present invention, this problem is solved by a method of the above mentioned type which is characterized in that it comprises the additional steps of:

providing a second urea synthesis reactor upstream of said stripping equipment;

connecting said second reactor with said stripping equipment;

providing means for recycling to said second reactor the second carbamate solution obtained in the recovery section.

In accordance with the present invention, it was surprisingly found that it is possible to further reduce steam consumption and further simplify the plant delegated to carry out the aforementioned process, by producing urea under high-yield conditions in the main reaction space (the major part in production terms) and low yield in the auxiliary reactor (minor part in production terms).

In accordance with the present invention, the above mentioned high-yield conversion conditions in the main reaction space may be achieved by feeding thereto the pure reagents and only the concentrated carbamate solution coming from the partial purification operations (partial decomposition of the carbamate, partial separation of the free ammonia and condensation) of the reaction mixture leaving the main reaction space.

In sharp contrast to the constant teaching of the prior art, the dilute carbamate solution coming from the urea separation and recovery section located downstream of both the main and auxiliary reaction spaces is recycled only and exclusively to the auxiliary reaction space.

The latter will then operate both in low-yield conditions because of the high quantity of water in the recycle solution and in low production terms.

In an alternative embodiment, the above-identified problem is solved by a method of the above mentioned type which is characterized in that it comprises the additional steps of:

providing a second urea synthesis reactor upstream of said stripping equipment;

providing means for recycling to said second reactor the second carbamate solution obtained in the recovery section;

connecting said second reactor with distillation equipment for subjecting a second reaction mixture leaving said second reactor to a treatment of partial decomposition of the carbamate and partial separation of the free ammonia in aqueous solution present in said second mixture;

providing means for recycling the vapors leaving said distillation equipment to said second reactor;

connecting said distillation equipment with the urea recovery section.

MODES FOR CARRYING OUT THE INVENTION

In accordance with a first embodiment of the present invention, the synthesis reaction in the main reaction space is carried out in accordance with the following process parameters;

| | |
|---|---|
| $NH_3/CO_2$ mol | 2.8–3.4, preferably 3.0 |
| $H_2O/CO_2$ mol | 0.1–0.25, preferably 0.18 |
| Reaction temperature | 180–195° C.; preferably 190° C. |
| Pressure | 140–155 bar; preferably 145 bar |
| $CO_2$ conversion yield | 69–71%. |

Advantageously, by operating with an ammonia/carbon dioxide molar ratio below 4 and preferably about 3, a reduction of the volume of the high-yield reaction space and of the heat requirement for preheating the reagents to the reaction temperature may be achieved.

The synthesis reaction in the auxiliary reaction space is carried out in accordance with the following process parameters:

| | |
|---|---|
| $NH_3/CO_2$ mol | 4.2–4.6; preferably 4.5 |
| $H_2O/CO_2$ mol | 1.2–1.6; preferably 1.5 |
| Reaction temperature | 180–192° C.; preferably 190° C. |
| Pressure | 140–155 bar; preferably 145 bar |
| $CO_2$ conversion yield | 56–60%. |

In accordance with this embodiment of the present invention, the reaction mixture leaving the auxiliary reaction space is subjected to a partial purification treatment (partial decomposition of the carbamate and partial separation of the free ammonia in aqueous solution) together with the reaction mixture leaving the main reaction space.

Advantageously, the purification treatment of the reaction mixture takes place at a temperature between 180 and 192° C. at inlet and between 165–170° C. at outlet of the treatment and at a pressure substantially equal to that existing in the main reaction space (140–155 bar) using feed carbon dioxide as the stripping agent.

Preferably, only partial condensation of the flow including ammonia and carbon dioxide in vapor phase obtained from the stripping operations with carbon dioxide is provided.

In this manner, part of the residual ammonia and carbon dioxide flow in vapor phase is fed to the auxiliary reaction space, so as to control the ammonia/carbon dioxide molar ratio within the above mentioned range and to close the overall heat balance of the reaction space.

The ammonia/carbon dioxide molar ratio in the auxiliary reaction space may also be controlled if necessary and held at an optimal value by feeding to this space essentially pure ammonia preferably taken from the ammonia feed.

In a preferred embodiment and again for the purpose of controlling the ammonia/carbon dioxide molar ratio within the above mentioned range and closing the overall heat balance, the above mentioned uncondensed residual flow of ammonia and carbon dioxide may also Be partly. fed to the main reaction space.

In another embodiment of the present invention, the reaction mixture leaving the auxiliary reaction space is subjected to distillation before being conveyed to the stripping treatment.

In this case, an advantageous reduction of the liquid flowrates sent to the stripping treatment to be subjected to partial purification and, along therewith, of the heating requirements to implement this treatment may be obtained.

By distilling this reaction mixture a flow including ammonia and carbon dioxide in vapor phase is obtained, which is recycled to the auxiliary reaction space for the purpose of controlling the ammonia/carbon dioxide molar ratio and achieving heat balance thereof.

Preferably, the step of distilling the reaction mixture leaving the auxiliary reaction space takes place at a pressure substantially equal to that existing in the auxiliary reaction space by fully conventional known procedures.

In accordance with the present invention, the conversion reaction of carbamate into urea in the auxiliary reaction space may take place either at a pressure substantially equal to that existing in the main reaction space or at a pressure of 4–8 bar lower.

In the former case, the ammonia, the carbon dioxide and the water present in vapor phase present in the vapor flows leaving the top of both reaction spaces, are absorbed by the dilute carbamate solution leaving the urea recovery section and are recycled in liquid phase to the auxiliary reaction space.

In the latter case, the vapors leaving the top of the main reaction space may be fed. into the auxiliary reaction space, so as to contribute to control the ammonia/carbon dioxide molar ratio within the latter.

Advantageously, furthermore, a certain simplification of the plant may be achieved, since the need of elevating the auxiliary reaction space with respect to the main one is eliminated.

In another embodiment of the present invention, the purification treatment of the reaction mixture takes place at a pressure substantially equal to that existing in the main reaction space (preferably 150 bar) under so-called isobaric—or "self stripping"—conditions.

The synthesis reaction in the main reaction space is carried out in accordance with the following process parameters:

| | |
|---|---|
| $NH_3/CO_2$ mol | 3.0–3.4; preferably 3.2 |
| $H_2O/CO_2$ mol | 0.08–0.2; preferably 0.1 |
| Reaction temperature | 185–195° C.; preferably 190° C. |
| Pressure | 145–155 bar; preferably 150 bar |
| $CO_2$ conversion yield | 70–73%. |

Again in this case, by operating with an ammonia/carbon dioxide molar ratio less than 4 and preferably about 3.2, there is an advantageous reduction both of the volume of the high yield reaction space and of the heat required for preheating the reagents to the reaction temperature.

The self-stripping treatment takes place at a temperature between 190 and 210° C.

The synthesis reaction in the auxiliary reaction space is carried out in accordance with the following process parameters:

| | |
|---|---|
| $NH_3/CO_2$ mol | 4.2–4.6; preferably 4.5 |
| $H_2O/CO_2$ mol | 1.0–1.5; preferably 1.3 |
| Reaction temperature | 185–195° C.; preferably 190° C. |
| Pressure | 145–155 bar; preferably 150 bar |
| Conversion yield $CO_2$ | 58–62%. |

Again in this embodiment of the present invention, the reaction mixture leaving the auxiliary reaction space is subjected to a partial purification treatment (partial decomposition of the carbamate and partial separation of the free ammonia in aqueous solution) together with the reaction mixture leaving the main reaction space.

Preferably, the process of the present invention provides, in this case also, a partial condensation of the flow including ammonia and carbon dioxide in vapor phase obtained by the isobaric stripping operations.

In this manner, the residual flow of ammonia and carbon dioxide in vapor phase is fed to the auxiliary reaction space so as to control the ammonia/carbon dioxide molar ratio within the above mentioned range and to close the synthesis reaction heat balance.

In this embodiment, moreover, the flow (including ammonia, carbon dioxide and water in vapor phase) leaving the top of the main reaction space is subjected to the isobaric stripping treatment together with the reaction mixture, while the flow leaving the top of the auxiliary reaction space is fed directly to the urea recovery section.

Similarly to the previous embodiment described hereinabove, the conversion reaction of the carbamate into urea may take place in the auxiliary reaction space either at a pressure substantially equal to that existing in the main reaction space or at a pressure 4–8 bar lower.

Preferably, the distillation step of the reaction mixture leaving the auxiliary reaction space takes place at a pressure between 135 and 155 bar, preferably 150 bar, and at a temperature between 190° and 210° C. with totally conventional known equipment and procedures.

Again in this case, an advantageous reduction of the liquid flowrates sent to the stripping treatment to be subjected to partial purification and, along therewith, of the heating requirements to implement this treatment may be obtained.

In accordance with another aspect of the present invention, the technical problem set forth above is solved by a plant obtainable by the above mentioned modernization method comprising:

a first urea synthesis reactor;
a stripping equipment for subjecting a first reaction mixture leaving said first reactor to a treatment of partial decomposition of the carbamate and partial separation of the free ammonia in aqueous solution present in said first mixture;
means for condensing at least partially the vapors leaving said stripping equipment and recycling a first carbamate solution to said first reactor;
a second reactor for urea synthesis in parallel with said first reactor;
a recovery section for separating the urea produced in said first and second reactor from a second aqueous solution of carbamate;
means for recycling the second carbamate solution obtained in the reaction space to said second reactor;
means for feeding a second reaction mixture leaving the second reactor to the stripping equipment.

In accordance with a still further embodiment of the invention, the above mentioned urea production plant comprises:

a first urea synthesis reactor;
a stripping equipment for subjecting a first reaction mixture leaving said first reactor to a treatment of partial decomposition of the carbamate and partial separation of the free ammonia in aqueous solution present in said first mixture;
means for condensing at least partially the vapors leaving said stripping equipment and recycling a first carbamate solution to said first reactor;
a second urea synthesis reactor in parallel with said first reactor;
a recovery section for separating the urea produced in said first and second reactor from a second aqueous solution of carbamate;
means for recycling the second carbamate solution obtained in the recovery section to said second reactor;
a distillation equipment for subjecting a second reaction mixture leaving said second reactor to a treatment of partial decomposition of the carbamate and partial separation of the free ammonia in aqueous solution present in the second mixture;
means for recycling the vapors leaving said distillation equipment to said second reactor.

In accordance with the present invention, the plants delegated to carry out the urea production process may be provided either new or by modifying pre-existing plants so as to obtain a production capacity expansion and at the same time an improved performance from the energy consumption viewpoint.

Further characteristics and advantages of the present invention are set forth in the detailed description of some preferred embodiments thereof, given below by way of non-limiting example with reference to the annexed drawings.

For the sole purpose of simplifying the discussion of the present invention, specific reference is made to the connecting ducts of the various parts of the plant described below and shown in the figures, conventional per-se, only where strictly necessary.

Figure 1:
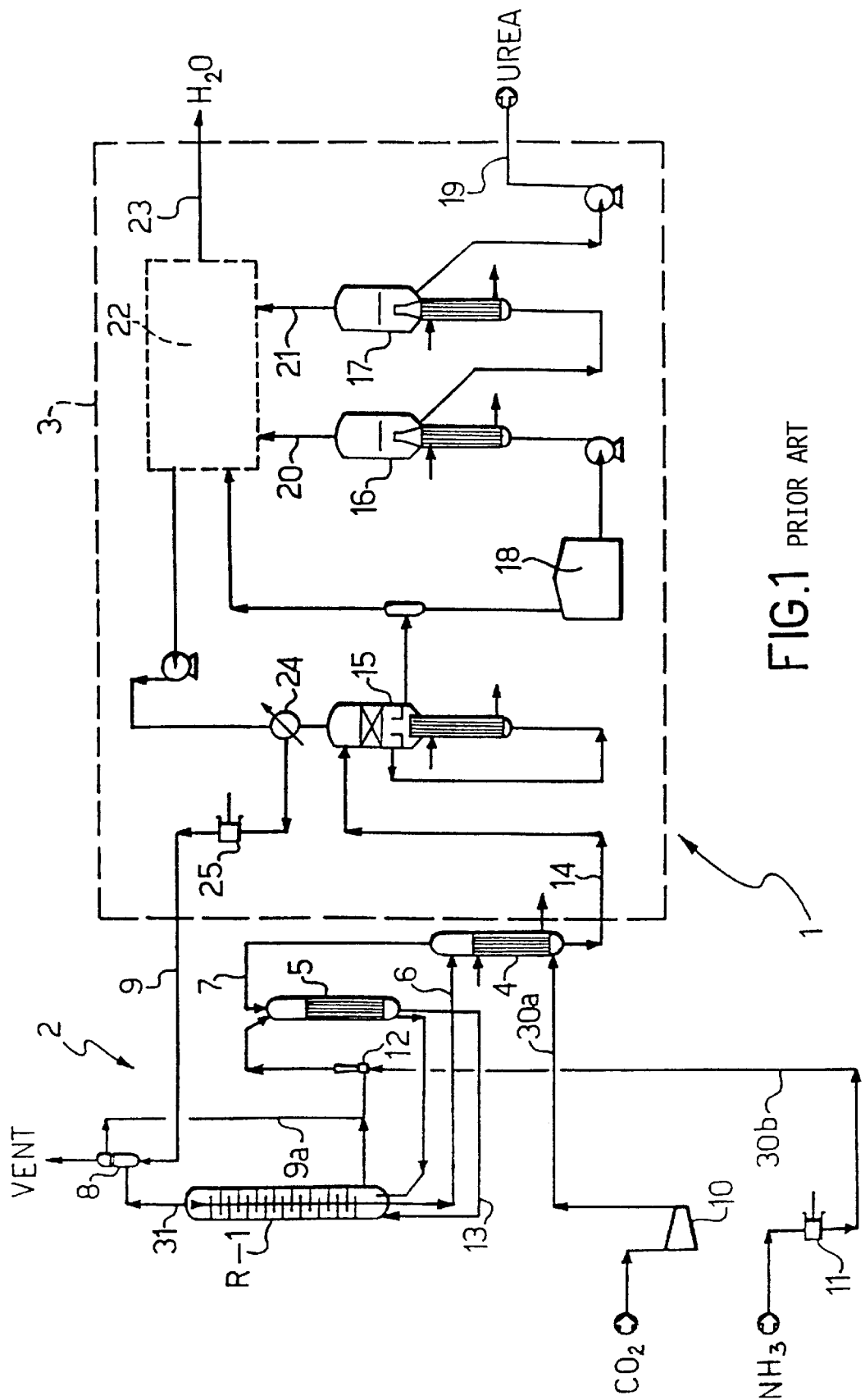
FIG. 1 shows schematically a plant in accordance with the prior art for urea production according to the so-called $CO_2$ stripping process.

With reference to FIG. 1, reference sign 1 indicates as a whole a urea production process of the so-called $CO_2$ stripping type in accordance with the prior art.

The plant 1 comprises a synthesis section 2 and a section 3 for purification and recovery of the urea produced and including in turn a number of pieces of equipment operating either at low pressure or vacuum, described more fully below.

The synthesis section 2 comprises, in series, a reactor R-1 for urea synthesis (in which is defined a respective reaction space), a high pressure stripper 4 for partial decomposition of the carbamate and partial separation of the free ammonia in aqueous solution present in the reaction mixture leaving R-1, and a carbamate condenser 5 for absorption of the stripping vapors with the ammonia feed and with a carbamate solution coming from-section 3.

The reactor R-1 is connected—at its bottom end and by means of a duct 6—with the stripper 4 from which outgoes a vapor phase (including ammonia, carbon dioxide and steam) sent to the carbamate condenser 5 through a duct 7 and a liquid phase (including a partially purified urea solution) sent to the recovery and purification section 3 through a duct 14.

The reactor R-1 is also connected—at the opposite top end and by means of a duct 31—with a scrubber 8 in which the vapors coming out of the reactor R-1 (including essentially ammonia, carbon dioxide and steam) are absorbed by means of a dilute solution of recycle carbamate coming from section 3 via duct 9.

Reference signs 10 and 11 indicate a centrifugal compressor and a high-pressure pump for sending the carbon dioxide to the stripper 4 and the ammonia feed to the carbamate condenser 5 via ducts 30a, 30b respectively.

An. ejector 12 sends to the carbamate condenser 5 either a recycle carbamate solution coming from the scrubber 8 through a duct 9a or an aqueous carbamate solution taken from the reactor R-1 near the bottom end thereof.

A duct 13 extending between the carbamate condenser 5 and the reactor R-1 allows recycling thereto an aqueous solution including the carbamate recycle as well as the ammonia and carbon dioxide feed.

As mentioned above, the duct 14 allows sending to the recovery section 3 a partially purified urea solution leaving the synthesis section 2.

The recovery section 3 comprises in turn a low-pressure distiller 15 (operating at approximately 3–4 bar) connected to a pair of conventional vacuum distillers 16, 17, in series, with the interposition of a urea solution collection tank 18.

Reference sign 19 indicates a duct for sending the purified urea leaving the section 3 to conventional finishing equipment not shown.

By reference signs 20 and 21 are indicated ducts for feeding ammonia-containing vapors to a vacuum section 22 in which these vapors are condensed in a known manner.

The condensates obtained and containing a certain quantity of residual ammonia are sent to a water treatment section via duct 23.

The vapors leaving the distiller 15 are combined with a dilute recovered ammonia solution coming from section 22 and are condensed at 24 and sent—as a dilute carbamate solution—to the scrubber 8 through a high-pressure pump 25 and the above mentioned duct 9.

With reference to the plant 1 described above, some embodiments of plants in accordance with the present invention, shown in FIGS. 2 through 4, will now be described.

In the following description and the figures, the parts of the plant 1 structurally or functionally equivalent to those discussed above with reference to FIG. 1 are indicated by the same reference signs and will not be further described.

Moreover, in accordance with a feature of the present invention, the following embodiments of the plant 1 either represent a brand new plant, or a plant obtained by modernizing a pre-existing plant as better explained below.

Figure 2:
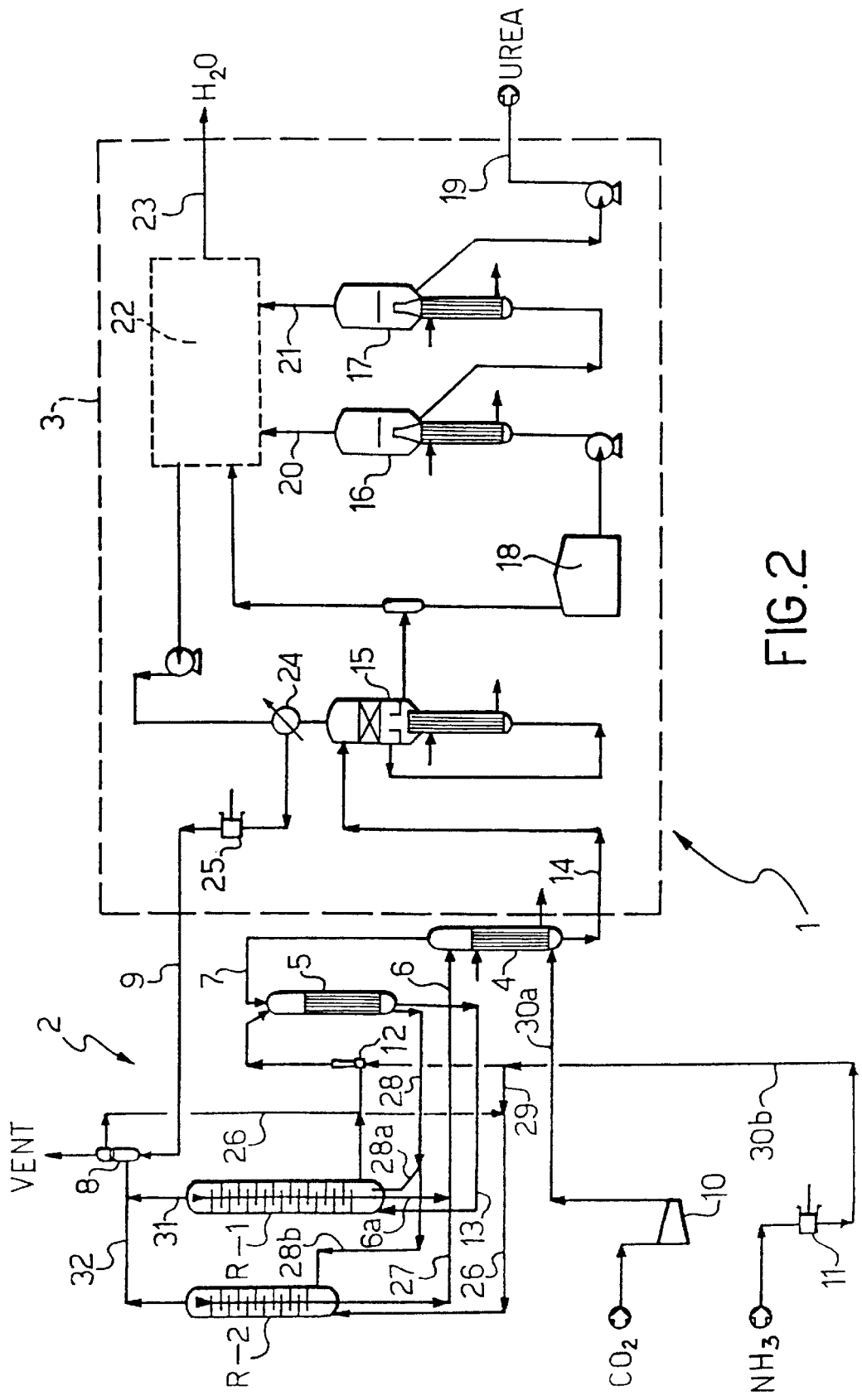
FIG. 2 shows schematically a first embodiment of a plant in accordance with the present invention, either as a brand new one or as obtained by modernizing the plant of FIG. 1.

With reference to FIG. 2 the synthesis section 2 of the plant 1 in accordance with the present invention further comprises a second urea synthesis reactor R-2 in parallel with reactor R-1.

In accordance with a feature of the present invention, reactor R-1 will act. as the main reactor, prevailing both in terms of yield and in terms of urea production, while reactor R-2 will act as the auxiliary reactor, minor both in terms of yield and in terms of urea production, since it is delegated to convert the dilute carbamate solution coming from the recovery section 3 into urea.

To this end, the plant 1 includes appropriate means, in this specific case a duct 26, for recycling the dilute carbamate solution leaving the scrubber 8 to the auxiliary reactor R-2.

In accordance with another feature of the present invention, the auxiliary reactor R-2 (in which is defined a respective reaction space) is connected through a duct 27 with the stripper 4 in which takes place a treatment of partial decomposition of the carbamate and partial separation of the free ammonia present in the reaction mixtures leaving both reactors R-1 and R-2.

Advantageously, the duct 27 extends between the auxiliary reactor (R-2) and a branch 6a of the duct 6 to allow considerable simplification of the plant.

In order to control the molar ratio $NH_3/CO_2$ and close the heat balances of the reactions in the main reactor R-1 and in the auxiliary reactor R-2, branches 28a, 28b of a duct 28 allow sending thereto part of the ammonia and carbon dioxide vapors not condensed in carbamate condenser 5.

Advantageously, the molar ratio $NH_3/CO_2$ and the heat balance in the auxiliary reactor R-2 may be further controlled by withdrawing part of the ammonia feed through a duct 29 extending between an ammonia feed duct 30b and the duct 26.

In accordance with a further feature of the present invention the bottom of the auxiliary reactor R-2 is positioned at a higher level with respect to ground than the bottom of the main reactor R-1, so as to facilitate feeding to R-2 of the uncondensed ammonia-rich vapors coming from carbamate condenser 5 via duct 28b.

Reference sign 32 indicates a duct for sending the vapors leaving the top of the auxiliary reactor R-2 to the scrubber 8.

As mentioned above, the plant 1 of FIG. 2 may be either a brand new plant or a plant obtained by modernizing a pre-existing plant such as that shown in FIG. 1.

Preferably, modernization. of the plant of FIG. 1 takes place by means of the steps of:
providing the auxiliary reactor R-2 upstream of the stripper 4 and in parallel with the existing reactor R-1;
connecting reactor R-2 with stripper 4 by means of duct 27;
providing duct 26 to recycle to reactor R-2 the dilute carbamate solution obtained in the recovery section 3 and leaving scrubber 8.

In accordance with the embodiment shown in FIG. 2, the auxiliary reactor R-2 is preferably arranged so that its bottom is provided at a higher level with respect to ground than the bottom of reactor R-1.

Preferably, the modernization method of the present invention also comprises the steps of providing the duct 28b for recycling to the reactor R-2 the ammonia-rich vapors not condensed in the carbamate condenser 5 and providing the duct 32 for sending to the scrubber 8 the vapors leaving the top of reactor R-2.

Figure 3:
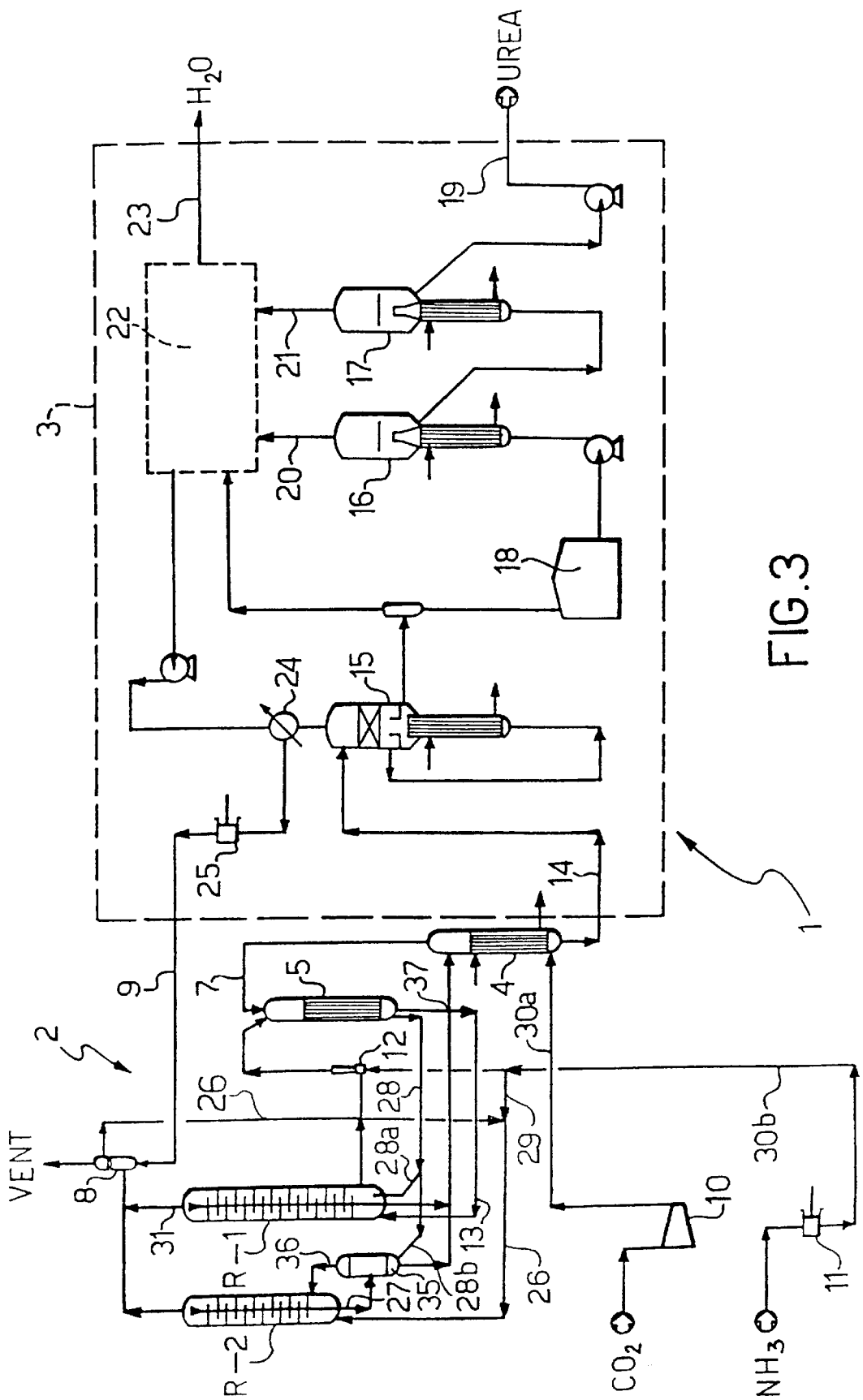
FIG. 3 shows schematically a second embodiment of a plant in accordance with the present invention, either as a brand new one or as obtained by modernizing the plant of FIG. 1.

In another embodiment of the plant 1 in accordance with the present invention, as shown in FIG. 3, the synthesis section 2 comprises a distiller 35 in which the reaction mixture leaving reactor R-2 via duct 27 is distilled, so as to generate a flow of ammonia-rich vapors recycled to the reactor R-2 through another duct 36.

The distiller 35 is in turn connected with the stripper 4 via duct 37 designed to feed the stripper with a reaction mixture partially purified by distillation.

Furthermore, in this embodiment of the plant 1, the uncondensed ammonia-rich vapors coming from carbamate condenser 5 are fed—through the branch 28b of duct 28—to distiller 35 and not to reactor R-2, so as to facilitate the distillation operations.

Advantageously, the distiller 35 allows to reduce the liquid flowrate (reaction mixture produced in R-2) sent to the stripper 4, with a reduction of the heat load of that equipment.

This feature is particularly advantageous when it is necessary to modernize a pre-existing plant in which the stripper is already operating at full capacity.

Figure 4:
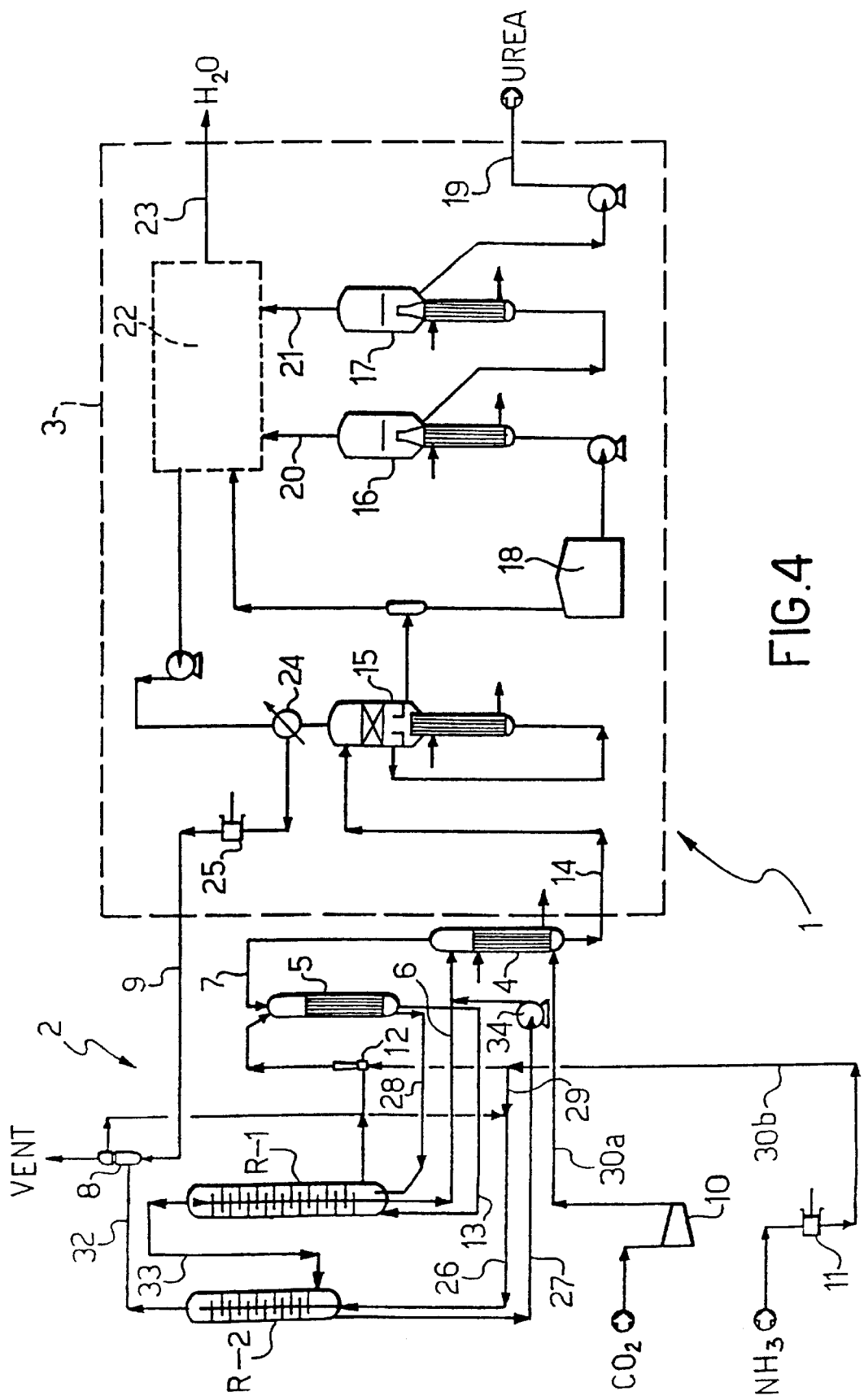
FIG. 4 shows schematically a third embodiment of a plant in accordance with the present invention, either as a brand new one or as obtained by modernizing the plant of FIG. 1.

In another embodiment of the plant 1 in accordance with the present invention, shown in FIG. 4, the bottom of the auxiliary reactor R-2 is at the same level as the bottom of the main reactor R-1 and in any case substantially at ground level, thus avoiding the works necessary to elevate reactor R-2, which are often complicated and costly.

In this case, the pressure in the auxiliary reaction space is reduced by 4–8 bar with respect to that existing in the primary reaction space.

In this embodiment, the molar ratio $NH_3/CO_2$ and the heat balance in the auxiliary reaction R-2 are controlled by sending to the latter the vapors leaving the top of the main reactor R-1 via duct 33, instead of withdrawing uncondensed vapors from the carbamate condenser 5.

In this case, duct 28 extends only between the carbamate condenser 5 and the main reactor R-1.

Because of the lower synthesis pressure existing in reactor R-2, the reaction mixture outgoing therefrom is sent to the stripper 4 by means of a pump 34 provided on the duct 27 upstream of that equipment.

Figure 5:
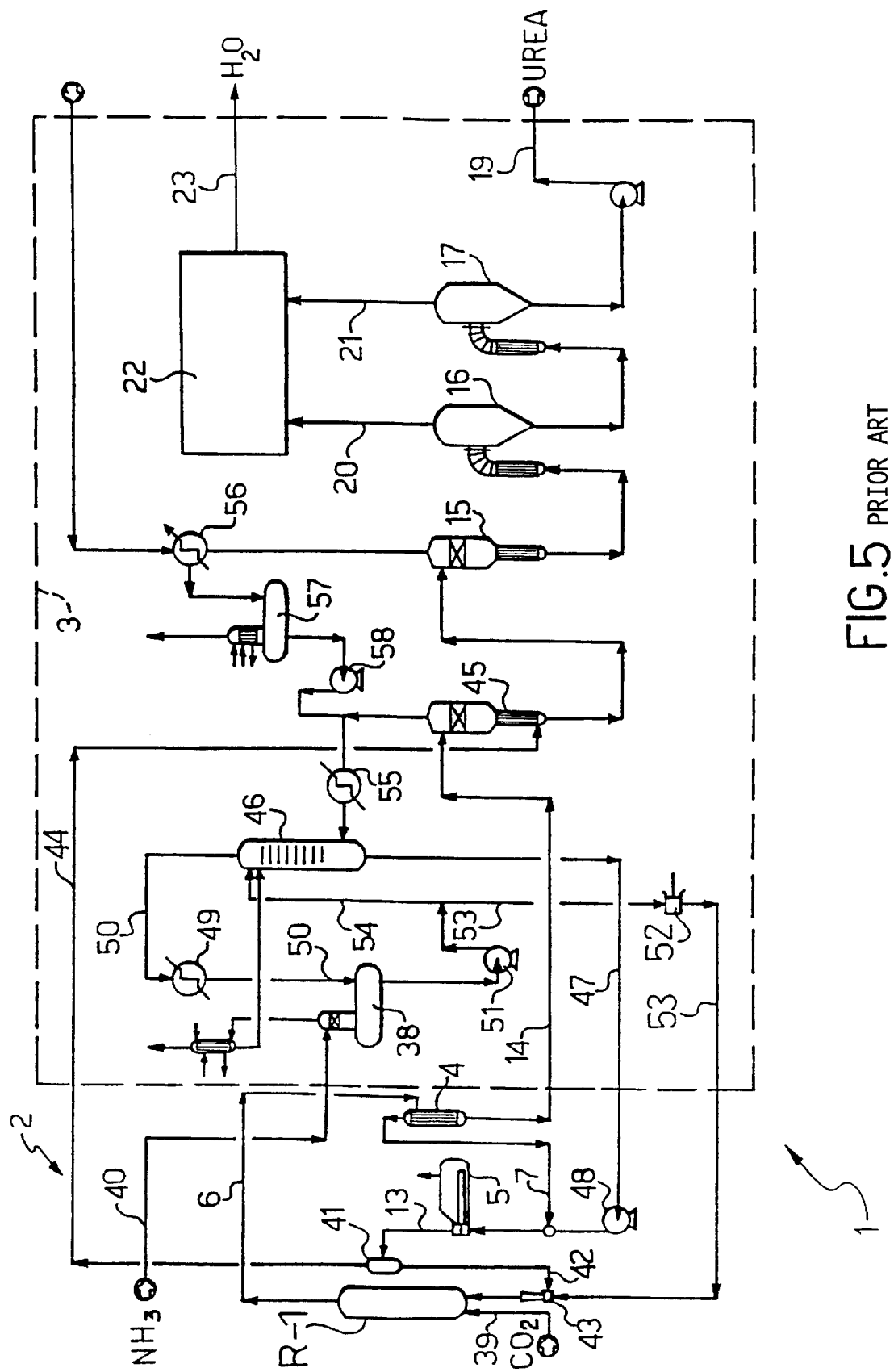
FIG. 5 shows schematically a plant in accordance with the prior art for urea production according to the so-called isobaric or self-stripping process.

With reference to FIG. 5, a urea production plant of the so-called isobaric stripping (self-stripping) type in accordance with the prior art, will be described below.

Again in this case, the, parts of plant 1 structurally or functionally equivalent to those discussed above with reference to FIGS. 1–4 are indicated by the same reference signs and will not be further described.

In the synthesis section 2 of the plant 1 of FIG. 5 and in accordance with conventional process conditions of self-stripping plants, the carbon dioxide and ammonia feed are sent directly to reactor R-1 and respectively to a collection tank 38, which is an integral part of the urea recovery section 3.

To this end, the plant 1 comprises appropriate ducts 39, 40 extending between a centrifugal compressor and a high-pressure pump (not shown) and the above mentioned reactor R-1 and tank 38.

In reaction section 2 there is also provided, downstream of carbamate condenser 5, a separator 41 designed to separate vapors including ammonia, carbon dioxide and steam not condensed in 5 from a carbamate solution recycled to reactor R-1 through a duct 42 and an ejector 43.

The vapors leaving the separator 41 are sent via duct 44 to a medium-pressure distiller 45 (operating at approximately 18 bar), provided in the recovery section 3 immediately downstream of the stripper 4.

The recovery section 3 comprises in this case, in addition to the above medium-pressure distiller 45, to the low-pressure distiller 15 and to the vacuum distillers 16, 17, a distillation column 46 designed to separate substantially pure ammonia from a dilute carbamate solution, both recycled to reactor R-1.

The dilute carbamate solution leaving the bottom of distillation column 46 is in particular recycled to carbamate condenser 5 via duct 47 and pump 48, while pure ammonia vapors leaving the top of column 46 are condensed in 49 and sent to the tank 38 through a duct 50.

The ammonia is thence recycled to R-1 together with fresh ammonia feed through pumps 51, 52 and a duct 53 on which ejector 43 is mounted.

Reference sign 54 indicates another duct extending downstream of the pump 51 and designed to feed to the column 46 an adequate liquid ammonia reflux for the rectification operations.

In the distillation column 46 is subjected to rectification a dilute carbamate solution obtained by condensing vapors leaving the top of the medium- and low-pressure distillers 45 and 15 in respective condensers indicated by 55 and 56.

The recovery section 3 also comprises a tank 57 in which is collected a dilute carbamate solution coming from condenser 56 and a pump 58 designed to feed this solution to the column 46.

With reference to the plant 1 of FIG. 5, some alternative embodiments of plants according to the present invention, shown in FIGS. 6 to 8, will now be described.

Figure 6:
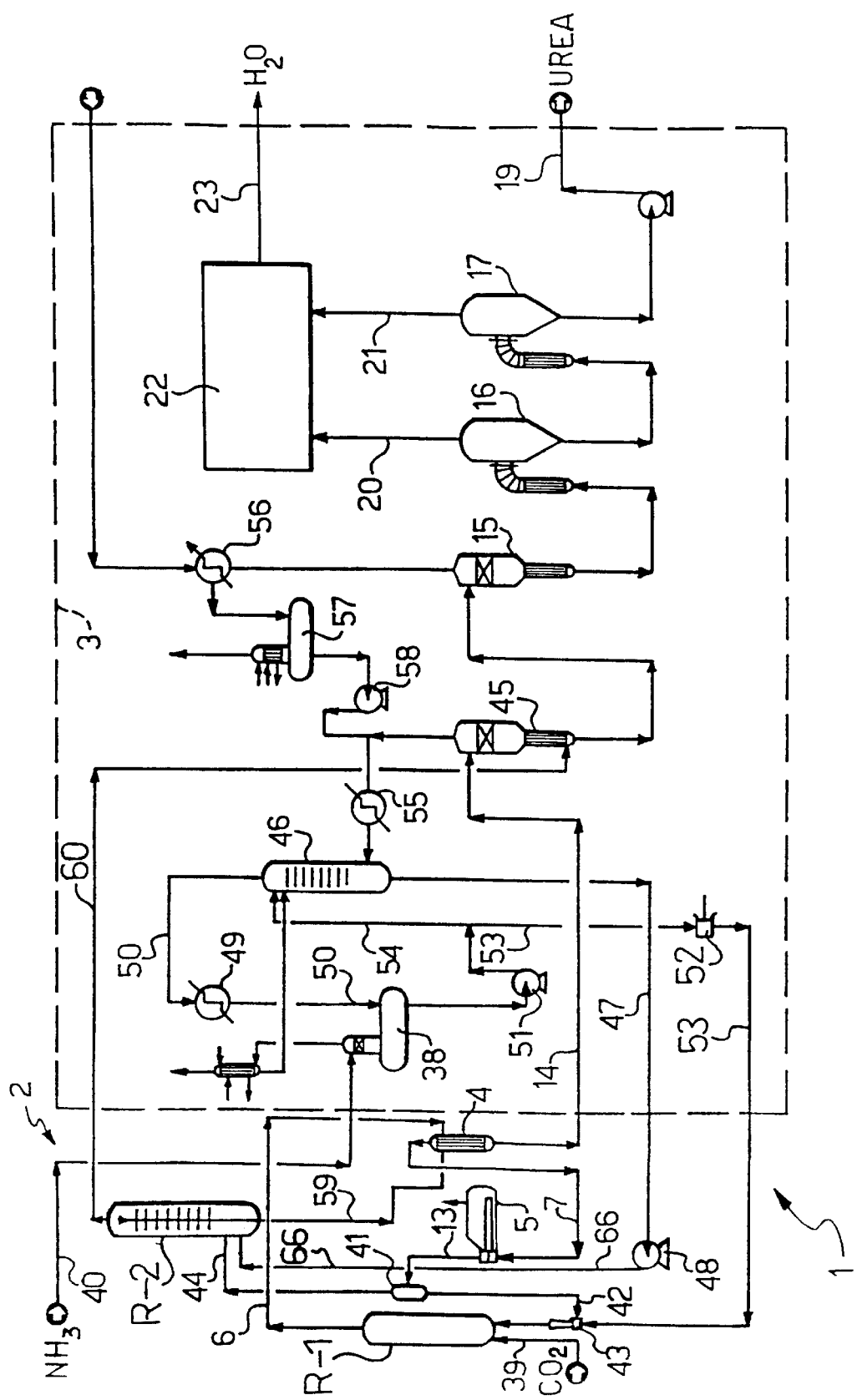
FIG. 6 shows schematically a fourth embodiment of a plant in accordance with the present invention, either as a brand new one or as obtained by modernizing the plant of FIG. 5.
Figure 7:
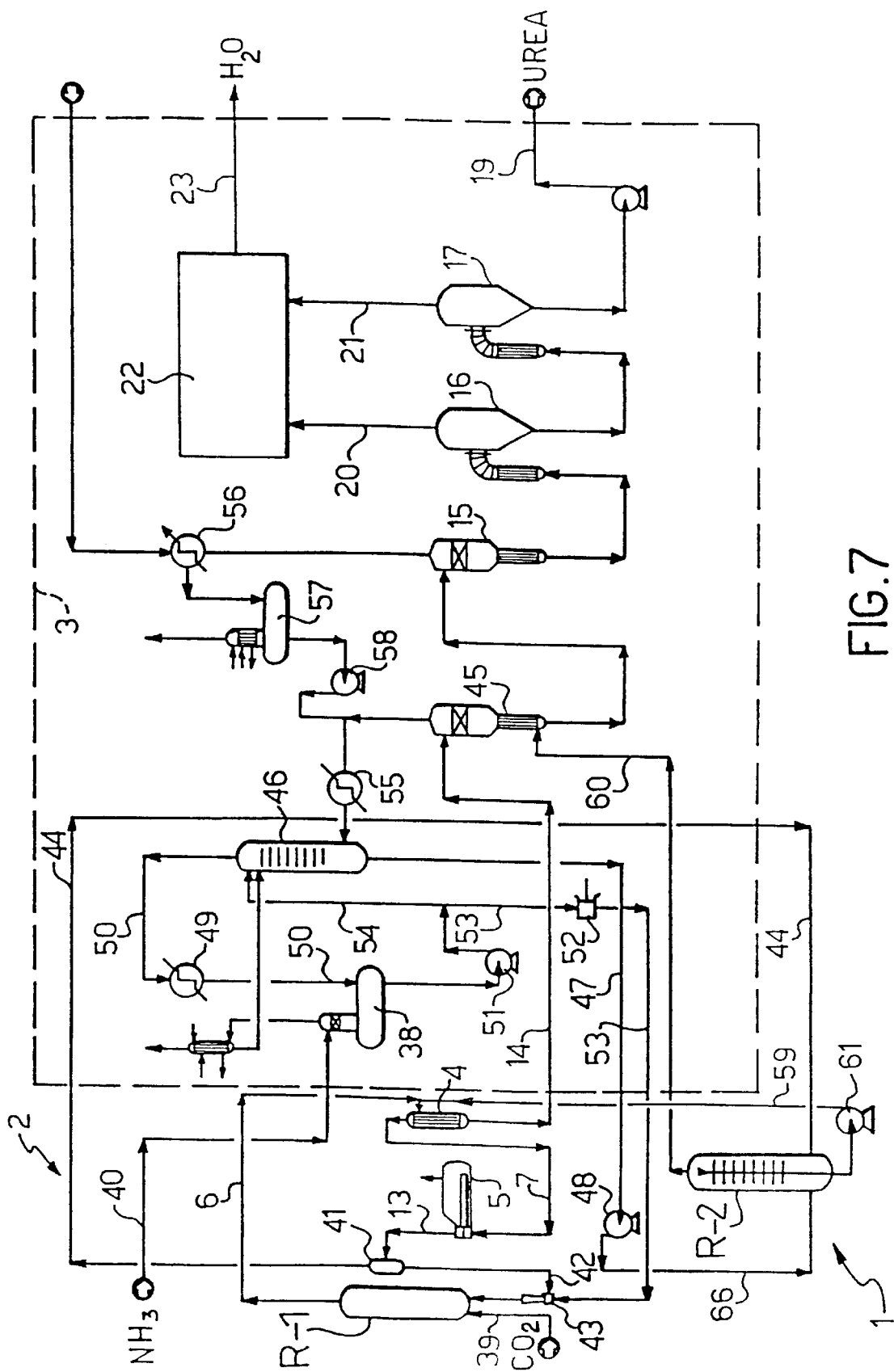
FIG. 7 shows schematically a fifth embodiment of a plant in accordance with the present invention, either as a brand new one or as obtained by modernizing the plant of FIG. 5.

With reference to FIG. 6, the synthesis section 2 of the plant 1 comprises a second urea synthesis reactor R-2 placed in parallel to reactor R-1.

Similarly to the previous embodiments of the invention described hereinabove, reactor R-1 acts as main reactor, prevailing both in terms of yield and production capacity, while reactor R-2 acts as auxiliary reactor, minor in both urea yield and urea production terms, the latter being delegated to convert into urea the dilute carbamate solution coming from the recovery section 3.

The plant 1 comprises appropriate means, in this specific case a duct 66, for recycling to the auxiliary reactor R-2 the dilute carbamate solution coming from the pump 48 and leaving the bottom of the distillation column 46.

The auxiliary reactor R-2 is in turn connected through a duct 59 with the stripper 4 in which take place a partial decomposition of the carbamate and partial separation of the free ammonia present in the reaction mixtures leaving reactors R-1 and R-2.

In order to control the molar ratio $NH_3/CO_2$ and the heat balance in the auxiliary reactor R-2, duct 44 now feeds this reactor with uncondensed ammonia-rich vapors leaving the carbamate condenser 5.

In this embodiment of the invention, the medium-pressure distiller 45 is fed with vapors leaving the top of auxiliary reactor R-2 through another duct 60.

Advantageously, the bottom of the auxiliary reactor R-2 is supported at higher level with respect to ground than the bottom of main reactor R-1, so as to facilitate feeding to R-2 the uncondensed vapors coming from separator 41.

The plant 1 of FIG. 6 may either be a brand new plant or a plant obtained by modernizing a pre-existing plant, such as that shown in FIG., 5, by means of a series of steps equivalent to those mentioned hereinabove with reference to the plant of FIG. 2.

In another embodiment of the plant 1 in accordance with the present invention, shown in FIG., 7, the auxiliary reactor R-2 is installed at a level lower than or equal to that of main reactor R-1, while the pressure in the auxiliary reaction space is reduced by 4–8 bar with respect to that existing in the primary reaction space.

Because of the lower synthesis pressure existing in reactor R-2, the reaction mixture outgoing therefrom is sent to stripper 4 by a pump 61 provided on duct 59 upstream of this equipment.

Again in this case, when the auxiliary reactor R-2 operates at a pressure lower than that of the main reactor R-1, it is possible to achieve plant simplification and a manufacture (or modernization) cost reduction of the plant 1.

Figure 8:
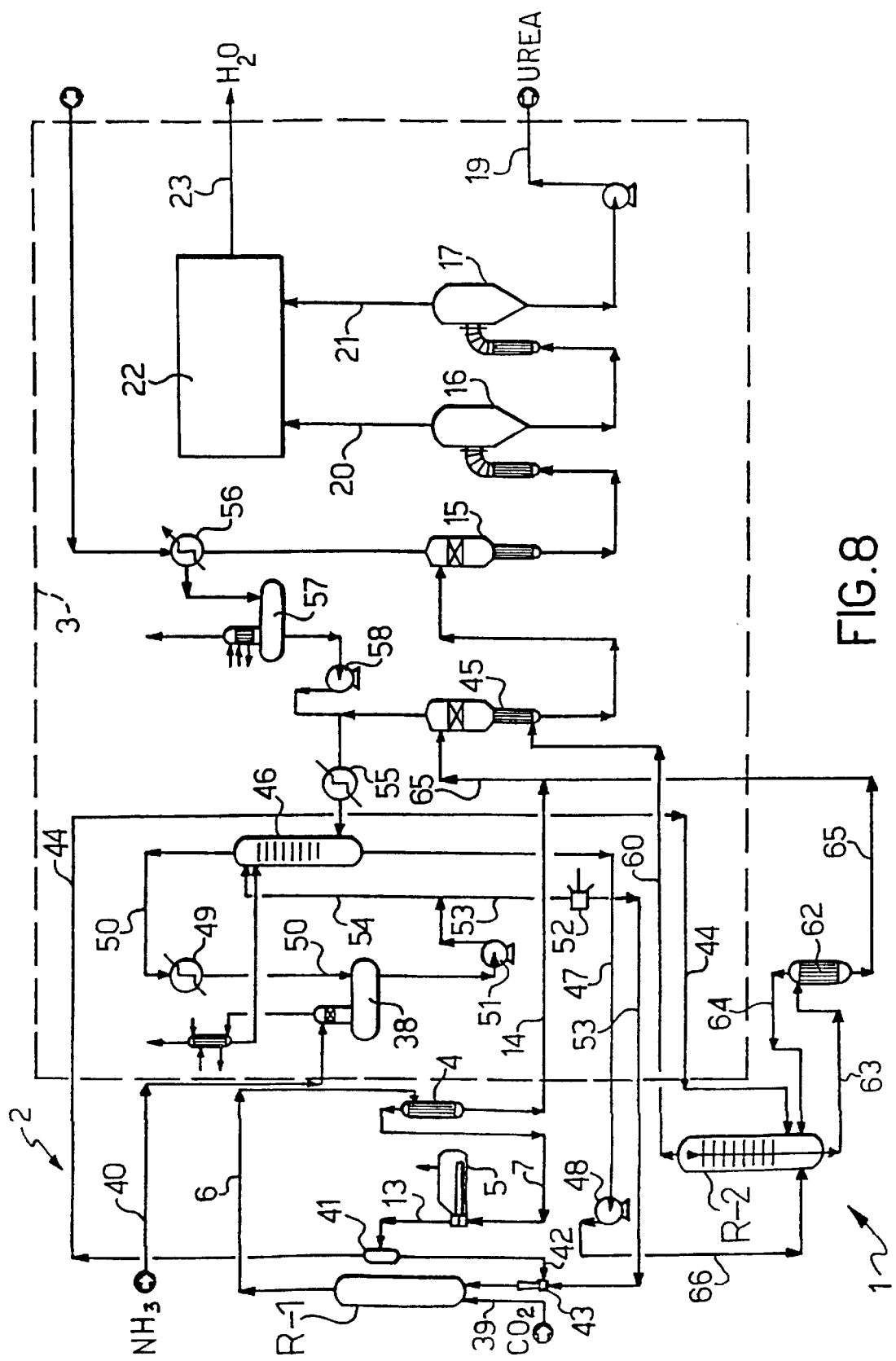
FIG. 8 shows schematically a sixth embodiment of a plant in accordance with the present invention, either as a brand new one or as obtained by modernizing the plant of FIG. 5.

In another embodiment of the plant 1 in accordance with the present invention, shown in FIG. 8, the synthesis section 2 comprises a distiller 62 in which the reaction mixture leaving reactor R-2 through a duct 63 is distilled, so as to generate a flow of ammonia-rich vapors recycled to the reactor R-2 through another duct 64.

The distiller 62 is in turn connected to the medium-pressure distiller 45 through a duct 65 designed to feed to the latter the distilled reaction mixture.

In this embodiment, the duct 65 is also used—in its terminal section—to convey to the medium-pressure distiller 45 the reaction mixture coming from the stripper 4 through duct 14.

Advantageously, the distiller 62 allows to reduce the liquid flowrate (reaction mixture produced in R-2) sent to the stripper 4, with a reduction of the heat load of this equipment.

This feature is particularly advantageous whenever it is desired to modernize a pre-existing plant in which the stripper is already operating at full capacity.

What is claimed is:

1. A method for modernizing a plant for urea production of the type comprising:
    a urea synthesis reactor (R-1);
    a stripping equipment (4) for subjecting a first reaction mixture leaving said reactor (R-1) to a treatment of partial decomposition of the carbamate and partial separation of the free ammonia in aqueous solution present in said first mixture;
    means (5) for condensing at least partially the vapors leaving said stripping equipment (4) and recycling a first carbamate solution to said reactor (R-1);
    a recovery section (3) for separating the urea produced in said reactor (R-1) from a second aqueous carbamate solution;
    characterized in that it comprises the steps of:
    providing a second urea synthesis reactor (R-2) upstream of said stripping equipment (4);
    connecting said second reactor (R-2) with said stripping equipment (4);
    providing means (9, 25, 26) for recycling to said second reactor (R-2) the second carbamate solution obtained in the recovery section (3); and
    providing a duct (33) for recycling to said second reactor (R-2) the vapors leaving the top of said first reactor (R-1).

2. A method according to claim 1, characterized in that said second reactor (R-2) is arranged with its bottom higher than the bottom of the first reactor (R-1).

3. A method according to claim 1, characterized in that it further comprises the step of providing means (8, 26) for condensing vapors leaving the top of said second (R-2) reactor and recycling the solution thus obtained to said second reactor (R-2).

4. A method for modernizing a plant for urea production of the type comprising:
    a urea synthesis reactor (R-1);
    a stripping equipment (4) for subjecting a first reaction mixture leaving said reactor (R-1) to a treatment of partial decomposition of the carbamate and partial separation of the free ammonia in aqueous solution present in said first mixture;
    means (5) for condensing at least partially the vapors leaving said stripping equipment (4) and recycling a first carbamate solution to said reactor (R-1);
    a recovery section (3) for separating the urea produced in said reactor (R-1) from a second aqueous carbamate solution;
    characterized in that it comprises the steps of:
    providing a second urea synthesis reactor (R-2) upstream of said stripping equipment (4);
    connecting said second reactor (R-2) with said stripping equipment (4);
    providing means (47, 48, 66) for recycling to said second reactor (R-2) the second carbamate solution obtained in the recovery section (3); and
    providing a duct (60) for feeding the vapors leaving the top of said second reactor (R-2) to said urea recovery section (3).

5. A method according to claim 4, characterized in that said second reactor (R-2) is arranged with its bottom higher than the bottom of the first reactor (R-1).

6. A method according to claim 4, characterized in that it further comprises the step of providing means (44) for recycling the uncondensed vapors coming from said stripping equipment (4) to said second reactor (R-2).

7. A method according to claim 4, characterized in that it further comprises the step of connecting the top of said second reactor (R-2) with a medium-pressure distiller (45) provided in the urea recovery section (3).

8. A method for modernizing a plant for urea production of the type comprising:
    a urea synthesis reactor (R-1);
    a stripping equipment (4) for subjecting a first reaction mixture leaving said reactor (R-1) to a treatment of partial decomposition of the carbamate and partial separation of the free ammonia in aqueous solution present in said first mixture;
    means (5) for condensing at least partially the vapors leaving said stripping equipment (4) and recycling a first carbamate solution to said reactor (R-1);
    a recovery section (3) for separating the urea produced in said reactor (R-1) from a second aqueous carbamate solution;

characterized in that it comprises the steps of:
  providing a second urea synthesis reactor (R-2) upstream of said stripping equipment (4);
  connecting said second reactor (R-2) with said stripping equipment (4);
  providing means (9, 25, 26) for recycling to said second reactor (R-2) the second carbamate solution obtained in the recovery section (3);
  connecting said second reactor (R-2) with a distillation equipment (35) for subjecting a second reaction mixture leaving said second reactor (R-2) to a treatment of partial decomposition of the carbamate and partial separation of the free ammonia in aqueous solution present in said second mixture;
  providing means (36) for recycling the vapors leaving said distillation equipment to said reactor (R-2);
  connecting said distillation equipment (35) with said stripping equipment (4); and
  providing means (28b) for recycling the uncondensed vapors coming from said stripping equipment (4) to said distillation equipment (35).

9. A method according to claim 8, characterized in that said second reactor (R-2) is arranged with its bottom higher than the bottom of the first reactor (R-1).

10. A method according to claim 8, characterized in that it further comprises the step of providing means (28a, 28b) for recycling the uncondensed vapors coming from said stripping equipment (4) to said second reactor (R-2).

11. A method according to claim 8, characterized in that it further comprises the step of providing means (8, 26) for condensing vapors leaving the top of said first (R-1) and/or second (R-2) reactor and recycling the solution thus obtained to said second reactor (R-2).

12. A method for modernizing a plant for urea production of the type comprising:
  a urea synthesis reactor (R-1);
  a stripping equipment (4) for subjecting a first reaction mixture leaving said reactor (R-1) to a treatment of partial decomposition of the carbamate and partial separation of the free ammonia in aqueous solution present in said first mixture;
  means (5) for condensing at least partially the vapors leaving said stripping equipment (4) and recycling a first carbamate solution to said reactor (R-1);
  a recovery section (3) for separating the urea produced in said reactor (R-1) from a second aqueous carbamate solution;
characterized in that it comprises the steps of:
  providing a second urea synthesis reactor (R-2) upstream of said stripping equipment (4);
  providing means (47, 48, 66) for recycling to said second reactor (R-2) the second carbamate solution obtained in the recovery section (3);
  connecting said second reactor (R-2) with distillation equipment (62) for subjecting a second reaction mixture leaving said second reactor (R-2) to a treatment of partial decomposition of the carbamate and partial separation of the free ammonia in aqueous solution present in said second mixture;
  providing means (64) for recycling the vapors leaving said distillation equipment (62) to said second reactor (R-2);
  connecting said distillation equipment (62) with said urea recovery section (3); and
  providing a duct (60) for feeding the top vapors leaving said second reactor (R-2) to said urea recovery section (3).

13. A method according to claim 12, characterized in that it further comprises the step of providing means (44) for recycling the vapors leaving said stripping equipment (4) to said second reactor (R-2).

14. A plant for urea production comprising:
  a first urea synthesis reactor (R-1);
  a stripping equipment (4) for subjecting a first reaction mixture leaving said first reactor (R-1) to a treatment of partial decomposition of the carbamate and partial separation of the free ammonia in aqueous solution present in said first mixture;
  means (5) for condensing at least partially the vapors leaving said stripping equipment (4) and recycling a first carbamate solution to said first reactor (R-1);
  a second urea synthesis reactor (R-2) in parallel with said first reactor (R-1);
  a recovery section (3) for separating the urea produced in said first (R-1) and second (R-2) reactors from a second aqueous carbamate solution;
  means (6a, 6) for feeding the first reaction mixture leaving said first reactor (R-1) to said stripping equipment (4);
  means (7) for feeding the vapors leaving said stripping equipment (4) to said means (5) for condensing;
  means (14) for feeding a urea solution produced in said stripping equipment (4) to said recovery section (3);
  means (9, 25, 26) for recycling the second carbamate solution obtained in the recovery section (3) to said second reactor (R-2);
  means (27, 34) for feeding a second reaction mixture leaving said second reactor (R-2) to said stripping equipment (4); and
  at least one duct (33) connecting the first and second reactors (R-1, R-2) for recycling to said second reactor (R-2) the vapors leaving the top of said first reactor (R-1).

15. A plant according to claim 14, characterized in that it further comprises means (10, 30a) for feeding a flow of feed carbon dioxide to said stripping equipment (4).

16. A plant according to claim 14, characterized in that the bottom of said second reactor (R-2) is higher than the bottom of the first reactor (R-1).

17. A plant according to claim 14, characterized in that it further comprises means (8, 26) for condensing vapors leaving the top of said second (R-2) reactor and recycling the solution thus obtained to said second reactor (R-2).

18. A plant according to claim 14, characterized in that it further comprises means (28) for recycling uncondensed vapors coming from said stripping equipment (4) to said first (R-1) reactor.

19. A plant for urea production comprising:
  a first urea synthesis reactor (R-1);
  a stripping equipment (4) for subjecting a first reaction mixture leaving said first reactor (R-1) to a treatment of partial decomposition of the carbamate and partial separation of the free ammonia in aqueous solution present in said first mixture;
  means (5) for condensing at least partially the vapors leaving said stripping equipment (4) and recycling a first carbamate solution to said first reactor (R-1);
  a second urea synthesis reactor (R-2) in parallel with said first reactor (R-1);

a recovery section (3) for separating the urea produced in said first (R-1) and second (R-2) reactors from a second aqueous carbarnate solution;

means (6a, 6) for feeding the first reaction mixture leaving said first reactor (R-1) to said stripping equipment (4);

means (7) for feeding the vapors leaving said stripping equipment (4) to said means (5) for condensing;

means (14) for feeding a urea solution produced in said stripping equipment (4) to said recovery section (3);

means (47, 48, 66) for recycling the second carbamate solution obtained in the recovery section (3) to said second reactor (R-2);

means (59, 61) for feeding a second reaction mixture leaving said second reactor (R-2) to said stripping equipment (4); and at least one duct (60) connecting the second reactor (R-2) and said urea recovery section (3) for feeding the vapors leaving the top of said second reactor (R-2) to said urea recovery section (3).

20. A plant according to claim 19, characterized in that the bottom of said second reactor (R-2) is higher than the bottom of the first reactor (R-1).

21. A plant according to claim 19, characterized in that it further comprises means (44) for recycling uncondensed vapors coming from said stripping equipment (4) to said second (R-2) reactor.

22. A plant for urea production comprising:

a first urea synthesis reactor (R-1);

stripping equipment (4) for subjecting a first reaction mixture leaving said first reactor (R-1) to a treatment of partial decomposition of the carbamate and partial separation of the free ammonia in aqueous solution present in said first mixture;

means (5) for condensing at least partially the vapors leaving said stripping equipment (4) and recycling a first carbamate solution to said first reactor (R-1);

a second urea synthesis reactor (R-2) in parallel with said first reactor (R-1);

a recovery section (3) for separating the urea produced in said first (R-1) and second (R-2) reactor from a second aqueous carbamate solution;

means (6a, 6) for feeding the first reaction mixture leaving said first reactor (R-1) to said stripping equipment (4);

means (7) for feeding the vapors leaving said stripping equipment (4) to said means (5) for condensing;

means (14) for feeding a urea solution produced in said stripping equipment (4) to said recovery section (3);

means (9, 25, 26) for recycling the second carbamate solution obtained in the recovery section (3) to said second reactor (R-2);

an equipment (35) for subjecting a second reaction mixture leaving said second reactor (R-2) to distillation to obtain a flow including ammonia and carbon dioxide in vapor phase and a partially purified reaction mixture;

means (27) for feeding the second reaction mixture leaving said second reactor (R-2) to said equipment (35) for distillation;

means (36) for recycling said flow including ammonia and carbon dioxide in vapor phase to said second reactor (R-2); and means (28b) for recycling uncondensed vapors leaving said stripping equipment (4) to said distillation equipment (35).

23. A plant according to claim 22, characterized in that it further comprises means (37) for feeding the partially purified reaction mixture leaving said distillation equipment (35) to said stripping equipment (4).

24. A plant according to claim 22, characterized in that it further comprises means (8) for condensing vapors leaving the top of said first (R-1) and/or second (R-2) reactor and recycling the solution thus obtained to said second reactor (R-2).

25. A plant for urea production comprising:

a first urea synthesis reactor (R-1);

stripping equipment (4) for subjecting a first reaction mixture leaving said first reactor (R-1) to a treatment of partial decomposition of the carbarnate and partial separation of the free ammonia in aqueous solution present in said first mixture;

means (5) for condensing at least partially the vapors leaving said stripping equipment (4) and recycling a first carbamate solution to said first reactor (R-1);

a second urea synthesis reactor (R-2) in parallel with said first reactor (R-1);

a recovery section (3) for separating the urea produced in said first (R-1) and second (R-2) reactor from a second aqueous carbamate solution;

means (6a, 6) for feeding the first reaction mixture leaving said first reactor (R-1) to said stripping equipment (4);

means (7) for feeding the vapors leaving said stripping equipment (4) to said means (5) for condensing;

means (14) for feeding a urea solution produced in said stripping equipment (4) to said recovery section (3);

means (47, 48, 66) for recycling the second carbamate solution obtained in the recovery section (3) to said second reactor (R-2);

an equipment (62) for subjecting a second reaction mixture leaving said second reactor (R-2) to distillation to obtain a flow including ammonia and carbon dioxide in vapor phase and a partially purified reaction mixture;

means (63) for feeding the second reaction mixture leaving said second reactor (R-2) to said equipment (62) for distillation;

means (64) for recycling said flow including ammonia and carbon dioxide in vapor phase to said second reactor (R-2); and a duct (60) connecting said second reactor (R-2) and said urea recovery section (3) for feeding the top vapors leaving said second reactor (R-2) to said urea recovery section (3).

26. A plant according to claim 25, characterized in that it further comprises means (65) for feeding the partially purified reaction mixture leaving said distillation equipment (62) to the urea recovery section (3).

27. A plant according to claim 25, characterized in that it further comprises means (44) for recycling the uncondensed vapors leaving said stripping equipment (4) to said second reactor (R-2).

* * * * *